United States Patent
Rubinstein et al.

(10) Patent No.: US 7,811,261 B2
(45) Date of Patent: Oct. 12, 2010

(54) NEEDLE COVER ASSEMBLY FOR A SYRINGE

(75) Inventors: Sergio Rubinstein, Buffalo Grove, IL (US); Samuel Kanosky Rosenberg, Orange Village, OH (US); Russell R. Stepke, Chicago, IL (US); Richard Mazursky, Riverwoods, IL (US); Todd Herlitz, Chicago, IL (US); Josh Harker, Elk Grove Village, IL (US); Mark W. Godfrey, Murrieta, CA (US); Stephen M. Jokela, Murrieta, CA (US)

(73) Assignee: STA-Med, LLC, Irvine, CA (US)

( * ) Notice: Subject to any disclaimer, the term of this patent is extended or adjusted under 35 U.S.C. 154(b) by 0 days.

(21) Appl. No.: 12/474,980

(22) Filed: May 29, 2009

(65) Prior Publication Data

US 2009/0299295 A1 Dec. 3, 2009

Related U.S. Application Data

(60) Provisional application No. 61/058,165, filed on Jun. 2, 2008, provisional application No. 61/138,786, filed on Dec. 18, 2008.

(51) Int. Cl.
*A61M 5/32* (2006.01)
(52) U.S. Cl. .................. 604/198; 604/263
(58) Field of Classification Search .............. 604/110, 604/192, 197, 198, 162, 263
See application file for complete search history.

(56) References Cited

U.S. PATENT DOCUMENTS

| | | | |
|---|---|---|---|
| 2,876,770 A | 3/1959 | White | |
| 3,134,380 A | 5/1964 | Armao | |
| 3,299,891 A * | 1/1967 | Smeton | 604/232 |
| 3,929,165 A | 12/1975 | Diebolt et al. | |
| 4,127,131 A | 11/1978 | Vaillancourt | |

(Continued)

FOREIGN PATENT DOCUMENTS

DE 20 2007 001 717 U1 7/2007

(Continued)

OTHER PUBLICATIONS

Smiths Medical, "Smiths Medical Wins $30 Million in Contracts for Safety Devices", Paul Harris—Director Communications, available online at: <http://www.smiths-medical.com/plugins/news/2008/may/30-million-contract.html>, May 29, 2008.

*Primary Examiner*—Melba Bumgamer
(74) *Attorney, Agent, or Firm*—Knobbe Martens Olson & Bear LLP (57) ABSTRACT

A single-use cover assembly that obscures a substantial majority or an entirety of an injection needle from view before, during, and after an injection procedure. The cover assembly includes a housing and a needle sleeve that retracts and extends by sliding axially within the housing. The needle sleeve carries a locking collar that moves from a first position to a second position once the needle sleeve is fully retracted. In the first position the locking collar allows retraction of the needle sleeve from a fully extended position. In the second position, a portion of the locking collar covers a tip of the needle, thereby preventing retraction of the needle sleeve from the fully extended position.

13 Claims, 10 Drawing Sheets

U.S. PATENT DOCUMENTS

| | | |
|---|---|---|
| 4,205,675 A | 6/1980 | Vaillancourt |
| 4,276,170 A | 6/1981 | Vaillancourt |
| 4,318,402 A | 3/1982 | Vaillancourt |
| 4,326,569 A | 4/1982 | Vaillancourt |
| 4,349,035 A | 9/1982 | Thomas et al. |
| 4,492,313 A | 1/1985 | Touzani |
| 4,511,359 A | 4/1985 | Vaillancourt |
| 4,525,157 A | 6/1985 | Vaillancourt |
| 4,525,374 A | 6/1985 | Vaillancourt |
| 4,585,435 A | 4/1986 | Vaillancourt |
| 4,610,683 A | 9/1986 | Vaillancourt |
| 4,617,012 A | 10/1986 | Vaillancourt |
| 4,636,200 A | 1/1987 | Vaillancourt |
| 4,636,313 A | 1/1987 | Vaillancourt |
| 4,645,495 A | 2/1987 | Vaillancourt |
| 4,652,256 A | 3/1987 | Vaillancourt |
| 4,655,750 A | 4/1987 | Vaillancourt |
| 4,678,462 A | 7/1987 | Vaillancourt |
| 4,682,607 A | 7/1987 | Vaillancourt |
| 4,704,177 A | 11/1987 | Vaillancourt |
| 4,723,955 A | 2/1988 | Vaillancourt |
| 4,725,267 A | 2/1988 | Vaillancourt |
| 4,743,243 A | 5/1988 | Vaillancourt |
| 4,773,458 A | 9/1988 | Touzani |
| 4,801,296 A | 1/1989 | Vaillancourt |
| 4,804,371 A | 2/1989 | Vaillancourt |
| 4,813,937 A | 3/1989 | Vaillancourt |
| 4,830,914 A | 5/1989 | Vaillancourt |
| 4,834,108 A | 5/1989 | Vaillancourt |
| 4,850,977 A | 7/1989 | Bayless |
| 4,850,996 A | 7/1989 | Cree |
| 4,863,431 A | 9/1989 | Vaillancourt |
| 4,867,743 A | 9/1989 | Vaillancourt |
| 4,894,055 A | 1/1990 | Sudnak |
| 4,904,248 A | 2/1990 | Vaillancourt |
| 4,943,281 A | 7/1990 | Kothe |
| 5,011,479 A | 4/1991 | Le et al. |
| 5,015,240 A | 5/1991 | Soproni et al. |
| 5,026,356 A | 6/1991 | Smith |
| 5,057,086 A | 10/1991 | Dillard, III et al. |
| 5,104,385 A | 4/1992 | Huband |
| 5,125,908 A | 6/1992 | Cohen |
| 5,279,584 A | 1/1994 | Dillard, III et al. |
| 5,292,314 A | 3/1994 | D'Alessio et al. |
| 5,295,975 A | 3/1994 | Lockwood, Jr. |
| 5,300,045 A | 4/1994 | Plassche, Jr. |
| 5,308,332 A | 5/1994 | Dillard, III et al. |
| 5,336,187 A | 8/1994 | Terry et al. |
| 5,348,544 A | 9/1994 | Sweeney et al. |
| 5,360,409 A | 11/1994 | Boyd, III et al. |
| 5,389,085 A | 2/1995 | D'Alessio et al. |
| 5,403,286 A | 4/1995 | Lockwood, Jr. |
| 5,423,765 A | 6/1995 | Hollister |
| 5,472,430 A | 12/1995 | Vaillancourt |
| 5,514,116 A | 5/1996 | Vaillancourt |
| 5,578,011 A | 11/1996 | Shaw |
| 5,582,597 A | 12/1996 | Brimhall et al. |
| 5,632,733 A | 5/1997 | Shaw |
| 5,651,480 A | 7/1997 | Piepenstock |
| 5,656,031 A | 8/1997 | Thorne et al. |
| 5,976,111 A | 11/1999 | Hart |
| 6,090,077 A | 7/2000 | Shaw |
| RE36,885 E | 9/2000 | Blecher et al. |
| 6,203,529 B1 | 3/2001 | Gabriel et al. |
| 6,468,383 B2 | 10/2002 | Kundel |
| 6,629,959 B2 * | 10/2003 | Kuracina et al. ............ 604/192 |
| 6,648,856 B1 | 11/2003 | Argento |
| 6,699,221 B2 | 3/2004 | Vaillancourt |
| 6,719,730 B2 | 4/2004 | Jansen et al. |
| 6,761,706 B2 | 7/2004 | Vaillancourt |
| 6,808,507 B2 | 10/2004 | Roser |
| 6,926,697 B2 | 8/2005 | Malenchek |
| 6,986,760 B2 | 1/2006 | Giambattista et al. |
| 7,083,600 B2 | 8/2006 | Meloul |
| 7,101,351 B2 | 9/2006 | Crawford et al. |
| 7,186,239 B2 * | 3/2007 | Woehr ................ 604/164.07 |
| 7,314,464 B2 | 1/2008 | Giambattista et al. |
| 7,361,160 B2 | 4/2008 | Hommann et al. |
| 2003/0114797 A1 | 6/2003 | Vaillancourt et al. |
| 2003/0144632 A1 | 7/2003 | Hommann et al. |
| 2004/0222579 A1 | 11/2004 | Adoline et al. |
| 2005/0267410 A1 | 12/2005 | Koska |
| 2005/0277893 A1 | 12/2005 | Liversidge |
| 2006/0189933 A1 | 8/2006 | Alheidt et al. |
| 2007/0060893 A1 | 3/2007 | Mahurkar |
| 2007/0265566 A1 * | 11/2007 | Simpson et al. ............ 604/110 |
| 2007/0293819 A1 | 12/2007 | Giambattista et al. |
| 2009/0227950 A1 | 11/2009 | Jensen et al. |
| 2010/0042053 A1 | 2/2010 | Dillard, III |

FOREIGN PATENT DOCUMENTS

| | | |
|---|---|---|
| GB | 732 313 | 6/1955 |
| WO | 02/09797 | 2/2002 |
| WO | 02/083205 | 10/2002 |
| WO | 03/066141 | 8/2003 |
| WO | 2004/069301 | 8/2004 |
| WO | 2004/069302 | 8/2004 |
| WO | 2004/110535 | 12/2004 |
| WO | WO 2006-029003 A2 | 3/2006 |
| WO | WO 2009/039022 A2 | 3/2009 |
| WO | WO 2010-019201 A1 | 2/2010 |

* cited by examiner

NEEDLE COVER ASSEMBLY FOR A SYRINGE

CROSS REFERENCE TO RELATED APPLICATIONS

This application claims the benefit of and priority to U.S. Provisional Patent Application Nos. 61/058,165 and 61/138,786 filed Jun. 2, 2008 and Dec. 18, 2008, respectively. The entire contents of each of these applications are hereby incorporated by reference.

BACKGROUND OF THE INVENTION

The present invention relates to needle covers and needle cover assemblies for syringes.

Syringes are used throughout the medical industry for the injection and withdrawal of a wide variety of fluids and solutions into and from the human body. Because of the numerous potential hazards associated with the handling and manipulation of bodily fluids, and particularly blood, there are a number of known safety features that are frequently incorporated into various types of syringes and syringe needles. For example, many syringe needles are provided with a removable cap that generally prevents needle sticks while the cover is in place. When the cap is removed the needle is exposed. These caps must be removed before an injection procedure and replaced after the injection procedure before discarding the needle. This removal and replacement procedure creates a risk of accidental needle sticks.

Syringes and syringe needles are also frequently configured such that at least the needles are disposable, that is, they are intended to be used only once and then thrown away. This procedure reduces the likelihood of transferring blood or tissue-born diseases from one patient to another. To this end, many syringe needles are configured to be quickly and easily detached from an appropriately configured syringe body. In this way, the syringe body may be reusable, and made of a relatively durable material, such as metal, while the disposable needle assemblies may be made of plastic or other similar, relatively inexpensive, materials.

SUMMARY OF THE INVENTION

In some embodiments, the invention provides a needle cover apparatus for attachment to a syringe needle. The needle defines an axis and includes a distal tip. The needle cover apparatus includes a base and a sleeve. The sleeve includes a distal end defining an opening and is supported by the base for movement between an extended position in which the sleeve covers the distal tip of the needle and a retracted position in which the distal tip extends through the opening. The needle cover apparatus also includes a locking member that is supported by at least one of the base and the sleeve. The locking member is moveable relative to the sleeve and includes a locking portion that moves into axial alignment with the distal tip and the opening in response to movement of the sleeve from the retracted position to the extended position. Movement of the locking portion into axial alignment with the distal tip and the opening prevents subsequent movement of the sleeve to the retracted position.

In other embodiments, the invention provides a needle cover apparatus for attachment to a syringe needle. The needle defines an axis and includes a distal tip. The needle cover apparatus includes a base and a sleeve that is supported by the base and that includes a distal end defining an opening. The sleeve is axially moveable only once relative to the needle from an extended position wherein the distal tip of the needle does not extend through the opening, to a retracted position wherein the distal tip extends through the opening, and back to the extended position. The sleeve is biased toward the extended position. The needle cover apparatus also includes a locking member that is moveable relative to the sleeve and that includes a locking portion that moves to cover the opening in response to movement of the sleeve from the retracted position to the extended position. When the locking portion moves to cover the opening it prevents subsequent movement of the sleeve to the retracted position.

In still other embodiments, the invention provides a needle cover apparatus for attachment to a syringe needle. The needle defines an axis and includes a distal tip. The needle cover apparatus includes a base that defines a central chamber. The central chamber receives a portion of the needle. The needle cover apparatus also includes a sleeve that is supported by the base and that is at least partially received by the central chamber. The sleeve defines a needle chamber that receives the needle. The sleeve also includes a distal end defining an opening that communicates with the needle chamber, and is axially moveable between an extended position in which the distal tip is positioned within the needle chamber and does not extend into the opening, and a retracted position wherein the distal tip extends through the opening. The sleeve is biased toward the extended position. The needle cover apparatus also includes a locking member that is received by the needle chamber and that includes a body portion through which the needle extends. The locking member includes a resilient arm that extends distally from the body portion, and a locking portion that is formed at an end of the arm. The locking member is moveable relative to the sleeve between a first position and a second position. When the sleeve is in the extended position and the locking member is in the first position, the locking portion is offset from the axis and positioned proximally of the distal tip. When the sleeve is moved from the extended position to the retracted position, the locking member moves from the first position to the second position. When the sleeve subsequently returns to the extended position with the locking member in the second position, the locking portion moves into alignment with the axis and is positioned distally of the distal tip, which prevents subsequent movement of the distal tip through the opening.

DETAILED DESCRIPTION

It is to be understood that the invention is not limited in its application to the details of construction and the arrangements of the components set forth in the following description or embodiments, or illustrated in the drawings. The invention is capable of other embodiments and of being practiced or being carried out in various ways. Also, it is to be understood that the phraseology and terminology used herein is for the purpose of description and should not be regarded as limiting.

Figure 1:
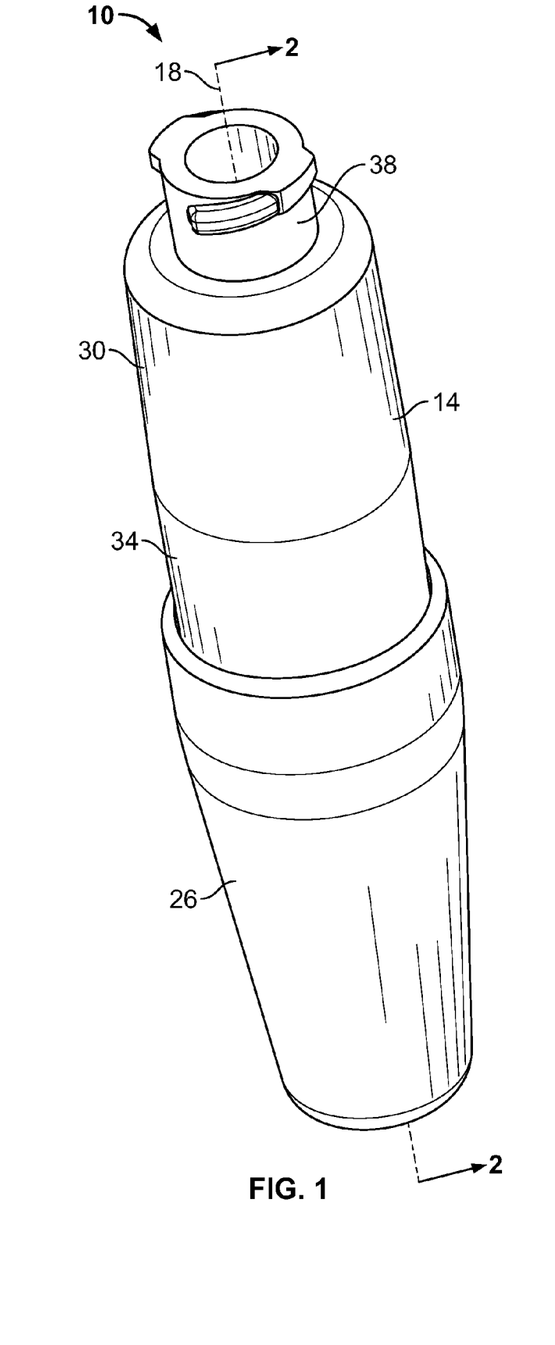
FIG. 1 is a perspective view of a needle and needle cover assembly.

FIG. 1 illustrates a needle cover assembly 10 that may be removably coupled to a standard or specially configured syringe assembly (not shown). The cover assembly 10 includes features and components, discussed below in detail, that generally hide the needle from view before, during, and after an injection procedure, thereby reducing or alleviating at least some anxiety or fear that might otherwise be felt by certain patients or other individuals upon seeing the exposed needle. The cover assembly 10 also includes features and components that prevent the cover assembly 10 and associated needle from being used more than once.

Although the illustrated cover assembly 10 is configured to be coupled to and removed from a syringe assembly, the cover assembly 10 may instead be integrally formed with the syringe assembly. In either case, the syringe assembly is generally of a known type suitable for the withdrawal and injection of fluids or other solutions from and into the body by way of the cover assembly 10. In the illustrated construction, the cover assembly 10 includes a base in the form of a generally cylindrical housing 14 that defines a central axis 18. The housing 14 defines or is coupled to a needle hub 22 that can be configured for either removable or permanent attachment to the syringe assembly, or that may be integrally formed with the syringe assembly. For example, the needle hub 22 may include internal or external threads or other suitable coupling, latching, or locking features such as tabs, slots, projections, pressure/snap fits, and the like, which may be provided in various combinations on various portions of the needle hub 22 for coupling to the syringe assembly. The coupling features engage corresponding features provided on the syringe assembly to removably couple the cover assembly 10 to the syringe assembly. Alternatively, the needle hub 22 may be permanently fixed (e.g. by sonic welding, adhesives, pressure/snap fits, or the like) or integrally formed with the syringe assembly. In the embodiment of FIG. 1, the cover assembly 10 also includes a one-piece, one-part cap 26 that is removably coupled to the housing 14. Other embodiments, discussed below, include multi-piece and/or multi-part caps that include a moveable or removable portion to assist in properly drawing a dose from a vial (see FIGS. 10-14).

Figure 2:
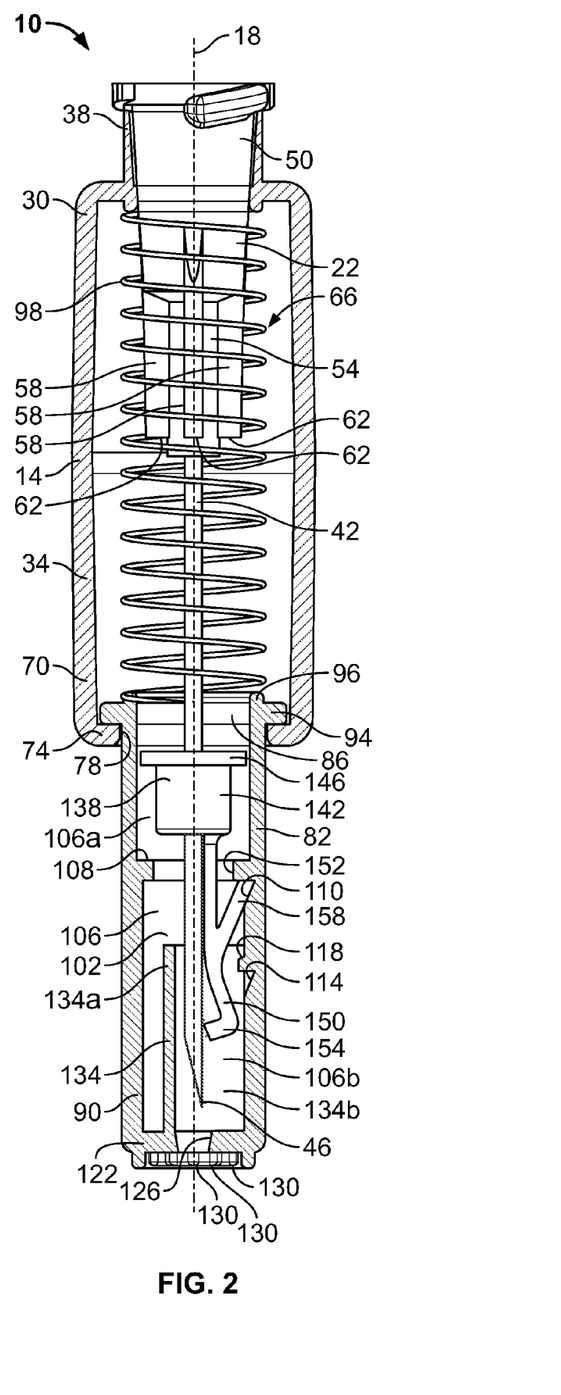
FIG. 2 is a plan view with portions illustrated in a section taken along line 2-2 of FIG. 1, and illustrating the needle and needle cover assembly with a cover removed and a needle sleeve and locking collar in a ready-for-use, first extended configuration.

FIG. 2 illustrates the cover assembly 10 in a ready-for-use configuration with the cap 26 removed. The housing 14 is illustrated in section in FIG. 2, revealing that the housing 14 includes upper and lower portions 30, 34 that are coupled to one another by a snap fit, coupling members, sonic welding, or other suitable forms of coupling, depending in part upon the specific material(s) of construction selected for the housing 14. In the illustrated construction, the upper portion 30 defines a generally cylindrical neck 38 that receives the needle hub 22, which may be a standard needle hub manufactured in mass quantity. In other constructions, the needle hub 22 and the upper portion 30 may be integrally formed with one another. Regardless of the specific construction of the needle hub 22, the needle hub 22 supports a needle 42 defining an axis and having a sharpened distal tip 46, which is generally configured for insertion into the skin or other tissue of the body. The needle 42 extends from and through the needle hub 22 for the transfer of fluid or other solutions between the syringe assembly, which may be or include a vial or ampoule and the tip 46.

The needle hub 22 includes a coupling portion 50 that engages the syringe assembly and the upper portion 30 of the housing 14, and a cylindrically reduced support portion 54 that extends axially from the coupling portion 50 and supports the needle 42. The support portion 54 also includes a plurality (e.g. four) of radially and axially extending ribs 58. Each rib 58 includes an axially-facing end surface 62 that is substantially normal to the central axis 18. The ribs 58 each have a substantially equal axial length, such that the end surfaces 62 lie in substantially the same plane.

The lower portion 34 of housing 14 cooperates with the upper portion 30 to define a central chamber 66. An end 70 of the lower portion 34 includes a radially inwardly extending shoulder 74 that defines an opening 78 that communicates with the chamber 66. The opening 78 slidingly receives a needle sleeve 82 that in turn receives and covers the needle 42. The needle sleeve 82 is substantially cylindrical and includes an inner end 86 positioned within the chamber 66 and an outer end 90. The inner end 86 includes a radially outwardly extending flange 94 that seats against the shoulder 74 of the lower portion 34. The inner end 86 also includes a substantially annular and axially extending rib 96 that locates a biasing member in the form of a spring 98. The spring 98 engages and extends between the inner end 86 of the needle sleeve 82 and the coupling portion 50 of the needle hub 22. The spring 98 biases the needle sleeve 82 toward an extended position (FIG. 2) in which the flange 94 of the needle sleeve 82 is biased into engagement with the shoulder 74 of the lower portion 34, and the needle sleeve 82 completely covers the needle 42. In one exemplary construction, the spring 98 is a linear spring having a free length of about 1.05 inches and a spring rate of about 0.7049 pounds per inch. Other constructions may include softer or stiffer springs depending on the application, and may be constructed of substantially any suitable material. Progressive springs and/or multiple springs of varying lengths may also be used to provide a variable effective spring rate during movement of the needle sleeve 82 between fully extended and fully retracted positions.

As shown in FIG. 1, the cap 26 covers the needle sleeve 82 until the cap 26 is removed from the housing 14, preferably just prior to an injection procedure. While in place, the cap 26 reduces or prevents contamination of the needle sleeve 82 and end 70 of the housing 14, for example during shipping and storage of the cover assembly 10. Unlike many other syringe assemblies, removing the cap 26 before an injection procedure does not expose the needle 42 because the needle 42 is covered by the needle sleeve 82, as shown in FIG. 2. Furthermore, once the cap 26 is removed it may immediately be discarded because the needle sleeve 82 also covers the needle 42 once the injection procedure is completed, as discussed further below.

The needle sleeve 82 includes an inner surface 102 that defines a generally cylindrical needle chamber 106. The needle chamber 106 is divided into an upper chamber 106a and a lower chamber 106b by a substantially annular wall 108 that extends radially inwardly from the inner surface 102. In the lower chamber 106b, the needle sleeve 82 defines a first, generally wedge-shaped recess 110 that is recessed with respect to the inner surface 102. The first recess 110 is positioned substantially adjacent the annular wall 108 and oriented such that the wider portion of the wedge shaped first recess 110 is nearer to the inner end 86 of the needle sleeve 82 and the narrow or pointed portion of the first recess 110 is nearer the outer end 90 of the needle sleeve 82.

The needle sleeve 82 also defines a second generally wedge-shaped recess 114 oriented similarly to the first recess 110 (e.g. the wide end is nearer the inner end 86 and the narrow end is nearer the outer end 90) and recessed with respect to the inner surface 102. The second recess 114 is axially spaced from the first recess 110 and positioned nearer the outer end 90 of the needle sleeve 82. The first and second recesses 110, 114 are substantially radially aligned with one another along the inner surface 102. The needle sleeve 82 also includes a ramp 118 that extends radially inwardly from the inner surface 102 and is positioned just above (as viewed in the Figures) the second recess 114.

The outer end 90 of the needle sleeve 82 includes an end wall 122 that closes the needle chamber 106 and defines an opening in the form of a central aperture 126 through which the needle 42 extends when the needle sleeve 82 is retracted, as discussed further below. A plurality of axially and radially extending ribs or projections 130 extend from the end wall and away from the needle chamber 106. In the illustrated construction, the projections 130 are arranged generally in the shape of an asterisk that is centered about the central aperture 126. During use, the projections 130 are configured to engage the skin or tissue of a patient just prior to the tip 46 of the needle 42 coming into contact with the skin or tissue of the patient. In this way, the projections 130 apply pressure to the skin or tissue that stimulates the patient's pressure-receptor nerves near the point of insertion of the needle 42. This stimulation of the pressure-receptor nerves competes or interferes with stimulation of the patient's pain receptor nerves upon insertion of the needle 42. In many patients, stimulation of the pressure-receptor nerves in this manner reduces the perception of pain during insertion of the needle 42.

While the illustrated needle sleeve 82 includes the projections 130 described above, a number of other configurations are possible, including a flat end surface, a beveled end surface, differently configured or arranged projections, and the like. The specific configuration of the outer end 90 generally will vary depending upon, among other things, the cover assembly's intended field of use (e.g., medical, dental, veterinary, and the like).

The outer end 90 of the needle sleeve 82 also includes a guide wall 134 that extends axially inwardly from the end wall 122. The guide wall 134 includes an arcuate portion 134a that partially encircles the central aperture 126, and a support portion 134b that extends radially from the arcuate portion 134a to the inner surface 102. The support portion 134b supports the arcuate portion 134a, and the arcuate portion 134a in turn supports and guides the needle 42 toward the central aperture 126 during retraction of the needle sleeve 82, as discussed further below.

The cover assembly 10 also includes a locking member in the form of a locking collar 138 that cooperates with the needle sleeve 82 to prevent more than a single use of the cover assembly 10, as discussed below. The locking collar 138 includes a generally cylindrical body 142 positioned in the upper chamber 106a and through which the needle 42 extends. The body 142 includes a radially outwardly extending flange 146 on one end, and an arm 150 on an opposite end. The arm 150 extends axially away from the body 142 through an aperture 152 in the annular wall 108 and into the lower chamber 106b. The arm 150 is radially offset from the central axis 18 and includes at its distal end a locking portion in the form of a foot 154 that, in the configuration of FIG. 2, engages a sidewall of the needle 42. Engagement of the foot 154 with the needle 42 bends the arm 150 such that the arm 150 diverges away from the central axis 18, with the arm being nearest the central axis 18 adjacent the body 142, and farthest from the central axis 18 adjacent the foot 154. The arm 150 is constructed of a suitably resilient material (e.g. plastic) and in a manner such that, in the configuration of FIG. 2, the foot 154 is biased into engagement with the needle 42 and the arm 150 seeks to return to a relaxed position in which the length of the arm is substantially parallel to the central axis 18.

The locking collar 138 also includes latching tab 158 that extends radially outwardly from the arm 154 between the body 142 and the foot 154. The latching tab 158 extends radially toward the inner surface 102 of the needle sleeve 82, and axially toward the body 142 of the locking collar 138. In the ready-for-use configuration of FIG. 2, the latching tab 158 is received by the first recess 110. The arm 150 and the latching tab 158 together have sufficient resiliency such that the locking collar 138 moves with the needle sleeve 82 as the needle sleeve 82 retracts during use, as discussed further below. The locking collar 138, including the body 142, flange 146, arm 150, foot 154, and latching tab 158 can be fabricated in one piece, and, if desired, from one uniform material, or may be fabricated from multiple pieces and, if desired, from different materials.

Figure 4:
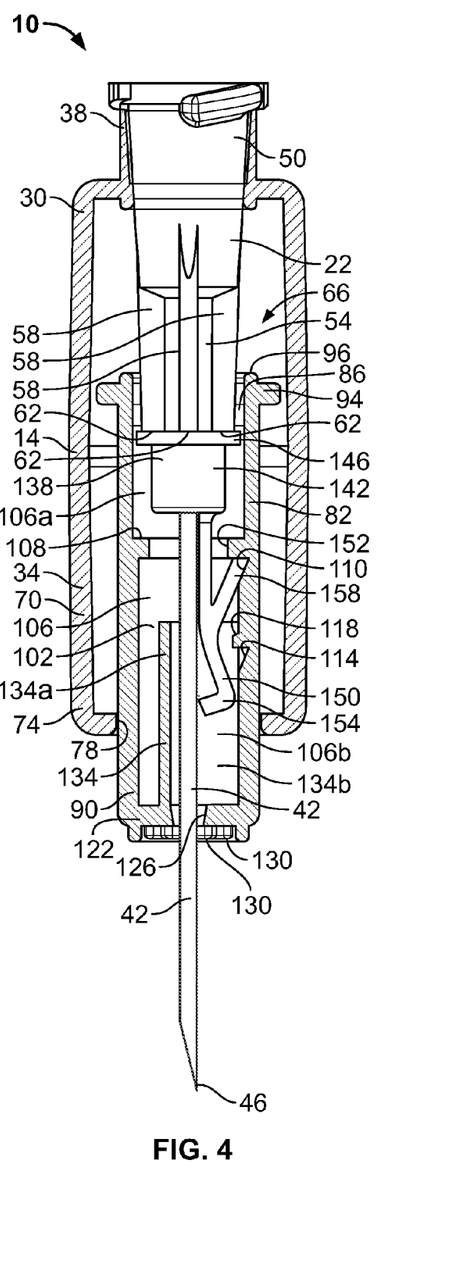
FIG. 4 is a plan view similar to FIG. 2 and illustrating the needle sleeve and locking collar in a second retracting position in which the locking collar has engaged a needle base.
Figure 5:
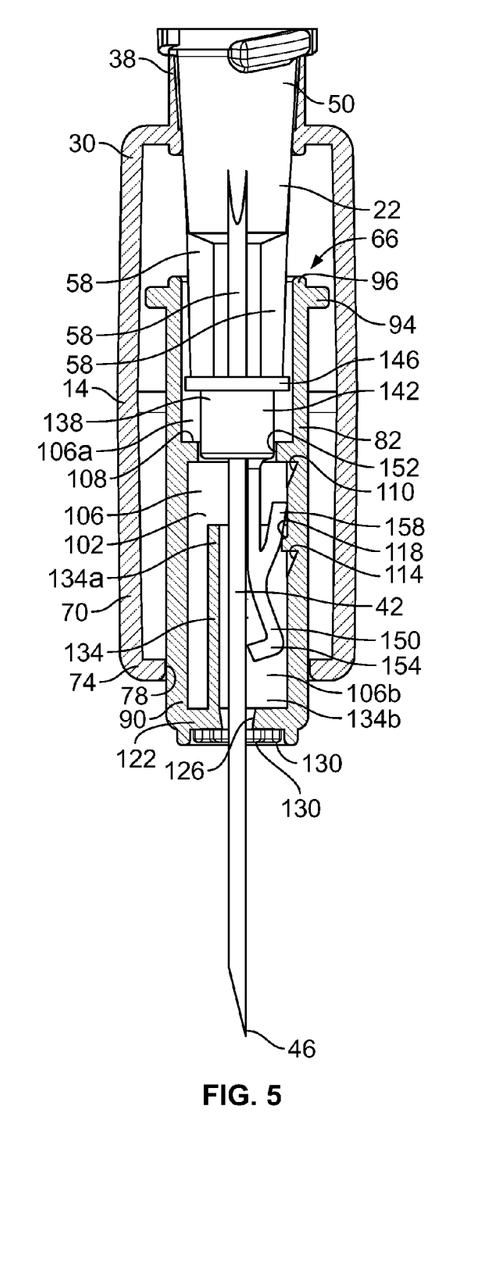
FIG. 5 is a plan view similar to FIG. 2 and illustrating the needle sleeve in a third retracting position in which the locking collar is still engaged with the needle base.
Figure 6:
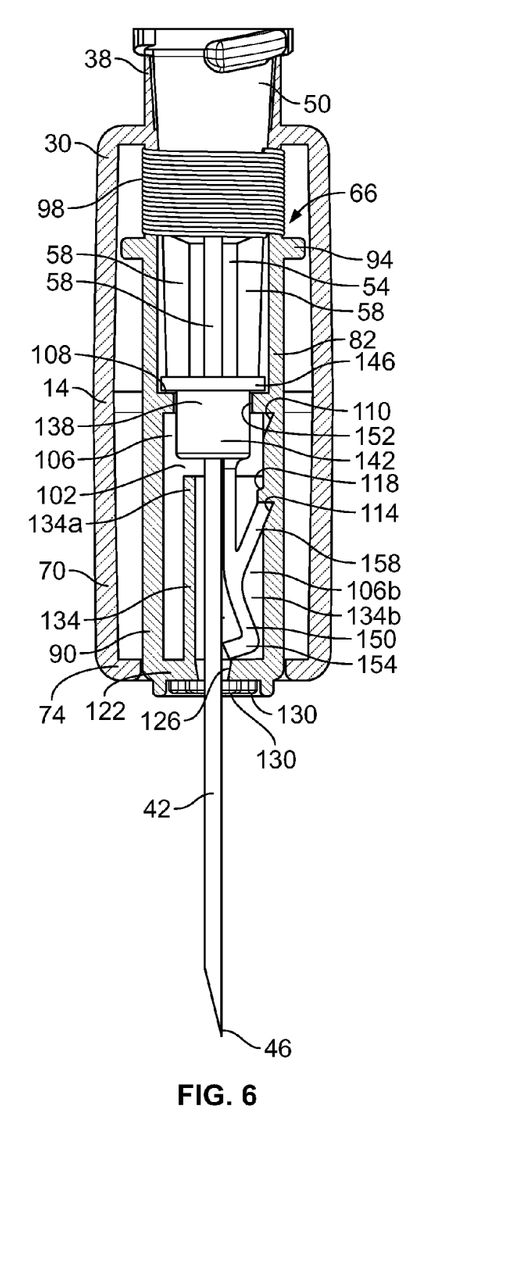
FIG. 6 is a plan view similar to FIG. 2 and illustrating the needle sleeve in a retracted position in which the locking collar has become coupled for axial movement with the needle sleeve.
Figure 7:
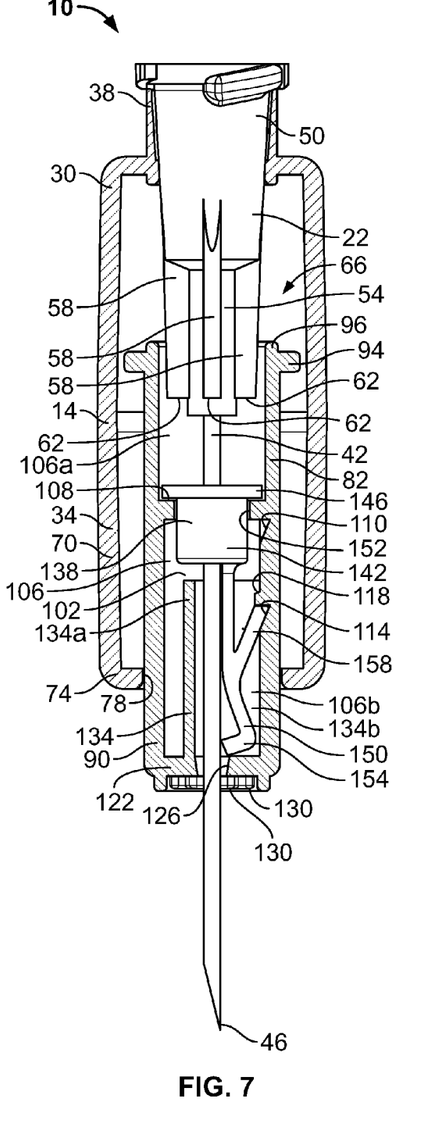
FIG. 7 is a plan view similar to FIG. 2 and illustrating the needle sleeve and locking collar in a first extending position.
Figure 8:
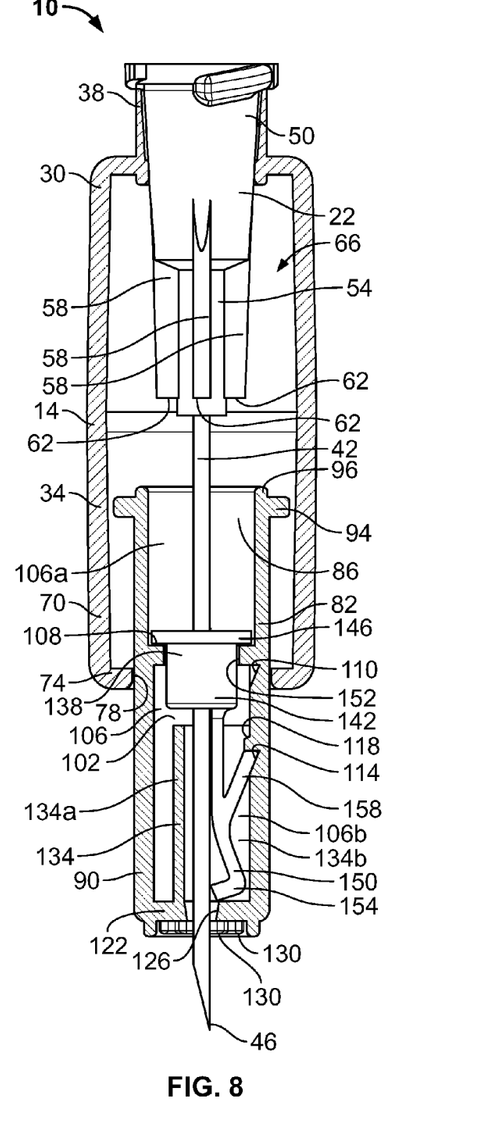
FIG. 8 is a plan view similar to FIG. 2 and illustrating the needle sleeve and locking collar in a second extending position.
Figure 9:
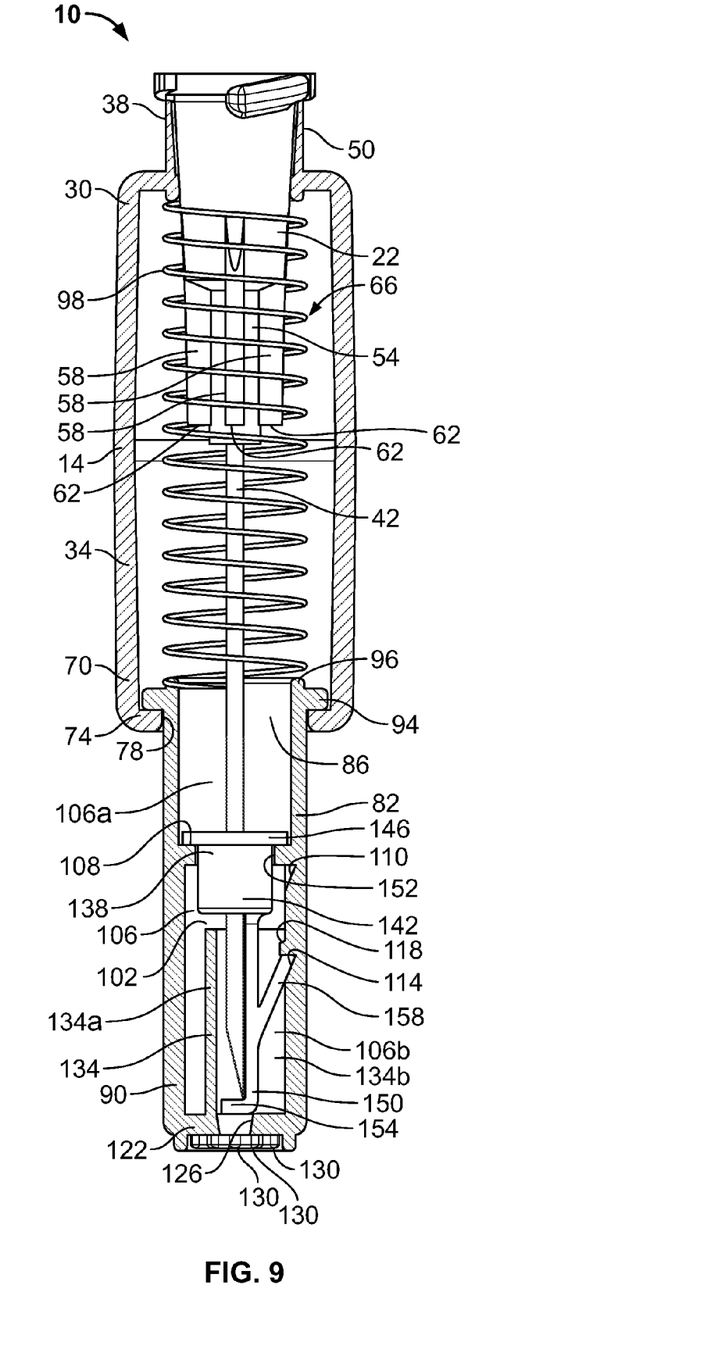
FIG. 9 is a plan view similar to FIG. 2 and illustrating the needle sleeve and locking collar in a use-prevention, second extended configuration.

FIGS. 3-9 illustrate the cover assembly 10 in various positions during an operating cycle that proceeds from the ready-for-use extended configuration shown in FIG. 2, to a fully retracted position shown in FIG. 6, and to a use-prevention extended configuration shown in FIG. 9. For clarity, the spring 98 is shown only in FIGS. 2, 6, and 9, which illustrate the spring in either its expanded or fully compressed state.

Before describing in detail the operation of the cover assembly 10 during an injection procedure, it should be noted that both the housing 14 and the needle sleeve 82 are preferably constructed of materials that are translucent, opaque, or otherwise optically distortive, such that the needle 42 is not visible to the patient before, during, or after the injection procedure. Furthermore, aside from the central aperture 126 through which the needle 42 extends during the injection procedure, the housing 14 and needle sleeve 82 are preferably devoid of slots, openings, or other apertures that would allow a patient to see into the housing 14 or needle sleeve 82 and view the needle 42. Thus, during an injection procedure, any portion of the needle 42 that does not extend through the central aperture 126 will be completely obscured from view by the housing 14 and needle sleeve 82, and any portion of the needle 42 that does extend through the central aperture 126 will be completely obscured from view because it is inside a vial or inside the patient. Of course, in some instances the entire needle 42 may not be completely obscured from view throughout the injection procedure depending upon, among other things, the specific shapes of the end wall 122 and the projections 130, and the angle at which the needle 42 is inserted into the vial and/or the patient's skin or tissue. Because many people become anxious simply at the sight of a needle, the above-described features can significantly reduce the anxiety or fear of the patient and/or the person administering the injection (who may also be the patient in cases of self-injection) to provide a more comfortable overall treatment experience.

To further reduce anxiety, particularly in children, the housing 14, cap 26, and needle sleeve 82 may be provided with a variety of indicia such as rainbows, balloons, cartoon characters, or other illustrations that are generally considered pleasing and comforting to children. In this way, a child patient may be allowed to choose from a variety of different cover assemblies 10 prior to an injection procedure. The cap 26, in addition or as an alternative to being colored or bearing indicia, may be fabricated to resemble a variety of different cartoon characters or other objects such that, upon removal from the housing 14 prior to an injection procedure, the cap 26 may be presented to a child patient as a distraction during the injection procedure. When fabricated to resemble a cartoon character or other object, the size and generally cylindrical shape of the cap 26 make it particularly well suited for use by the child as a finger puppet. Each of these features provides the opportunity to reduce the anxiety or fear experienced by many children before, during, and after an injection procedure.

Figure 3:
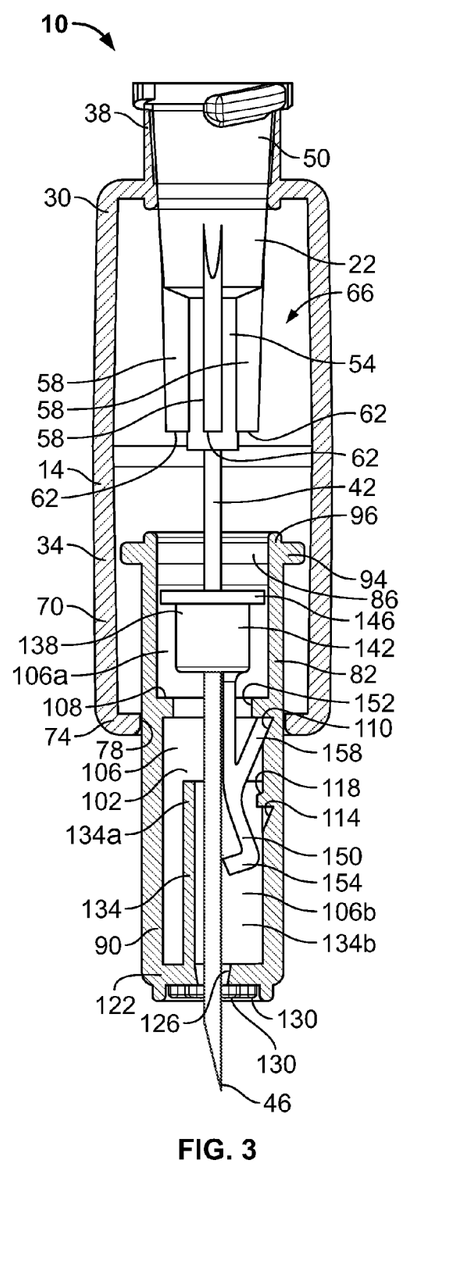
FIG. 3 is a plan view similar to FIG. 2 and illustrating the needle sleeve and locking collar in a first retracting position.

FIG. 3 illustrates the cover assembly 10 in a first retracting position in which the needle sleeve 82 is partially retracted relative to the needle 42 and the housing 14. The position of FIG. 3 is generally associated with a point shortly after the needle tip 46 has pierced the septum of a vial or the skin or tissue of the patient. The locking collar 138 moves together with the needle sleeve 82 toward the needle hub 22 due to engagement between the latching tab 158 and the first recess 110 in the needle sleeve 82, which maintains the locking collar 138 in a first position relative to the needle sleeve 82. FIG. 4 illustrates the cover assembly 10 in a second retracting position in which the needle sleeve 82 is further retracted relative to the needle 42 and the housing 14, and the flange 146 of the locking collar 138 has engaged the end surfaces 62 of the ribs 58 provided on the support portion 54 of the needle hub 22. Engagement of the locking collar 138 with the end surfaces 62 of the ribs 58 prevents further axial movement of the locking collar 138 toward the needle hub 22.

As shown in FIG. 5, continued retraction of the needle sleeve 82 beyond the position illustrated in FIG. 4 results in relative axial movement between the needle sleeve 82 and the locking collar 138. Specifically, because the end surfaces 62 of the ribs 58 prevent further axial movement of the locking collar 138, further retraction of the needle sleeve 82 disengages the latching tab 158 from the first recess 110 and moves the locking collar 138 away from the first position relative to the needle sleeve 82. As the locking collar 138 moves axially relative to the needle sleeve 82, the latching tab 158 slides along the inner surface 102 of the needle sleeve 82 until it engages the ramp 118, as shown in FIG. 5. The resilient nature of the arm 150 and the latching tab 158 provides resistance to radially inward movement of the latching tab 158 upon engagement with the ramp 118. This in turn provides a slight but noticeable resistance to further axial movement of the needle sleeve 82. The ramp 118 and the corresponding resistance to axial movement are provided so that a user who is withdrawing fluid or solution from a vial or other container for subsequent injection knows to stop inserting the needle 42 into the vial. By stopping at the position illustrated in FIG. 5, withdrawing the dose with the syringe, and subsequently removing the needle 42 from the vial, the user avoids moving the locking collar 138 into a locked position that would otherwise prevent subsequent use of the cover assembly 10 to inject the withdrawn dose into a patient.

As shown in FIG. 6, the needle sleeve 82 is substantially fully retracted within the housing 14 and the latching tab 158 has moved into engagement with the second recess 114 in the needle sleeve 82, such that the locking collar 138 is in a second position relative to the needle sleeve. Furthermore, the flange 146 of the locking collar 138 is engaged with the annular wall 108 of the needle sleeve 82, thereby coupling the locking collar 138 for axial movement with the needle sleeve 82 in both axial directions.

As shown in FIGS. 7 and 8, as the needle sleeve 82 extends from the housing 14 (e.g., as the needle 42 is withdrawn from the patient), the locking collar 138 moves axially therewith. It should be noted that throughout the range of motion illustrated in FIGS. 2-8, the foot 154 of the locking collar 138 slides along the outer surface of the needle 42, and deflection of the needle 42 away from the central axis 18 as a result thereof is at least partially restrained by the guide wall 134.

As the needle sleeve 82 extends from the housing toward the position illustrated in FIG. 9, the foot 154 moves distally beyond the tip 46 of the needle 42 and the biasing force provided by the resiliency of the arm 150 urges the foot 154 into the use-prevention position illustrated in FIG. 9. In the use-prevention position, the foot 154 moves into axial alignment with the distal tip 46 of the needle 42. Because the locking collar 138 is axially fixed relative to the needle sleeve 82, the foot 154 also prevents retracting movement of the needle sleeve 82 by engaging the tip 46 of the needle 42 if the needle sleeve 82 is moved in a retracting direction. The foot 154 also overlies the central aperture 126 of the needle sleeve 82 to reduce or prevent the dripping of fluids from the needle sleeve 82. Thus, it can be observed that the features and components associated with locking the needle sleeve 82 in the extended position after an injection procedure (e.g., the locking collar 138, including the body 142, flange 146, arm 150, foot 154, and latching tab 158, and the first and second recesses 110, 114) are internal to the housing 14 and the needle sleeve 82.

FIGS. 10-14 illustrate an alternative embodiment of the cover assembly 10 that is identified as cover assembly 10a in FIGS. 10-14. The features and components of the cover assembly 10a are similar in form and function to those described above with respect to the cover assembly 10, and have been provided with like numerals. To the extent components of the assembly 10a differ slightly from those of the assembly 10, such differences are described and explained below.

Figure 10:
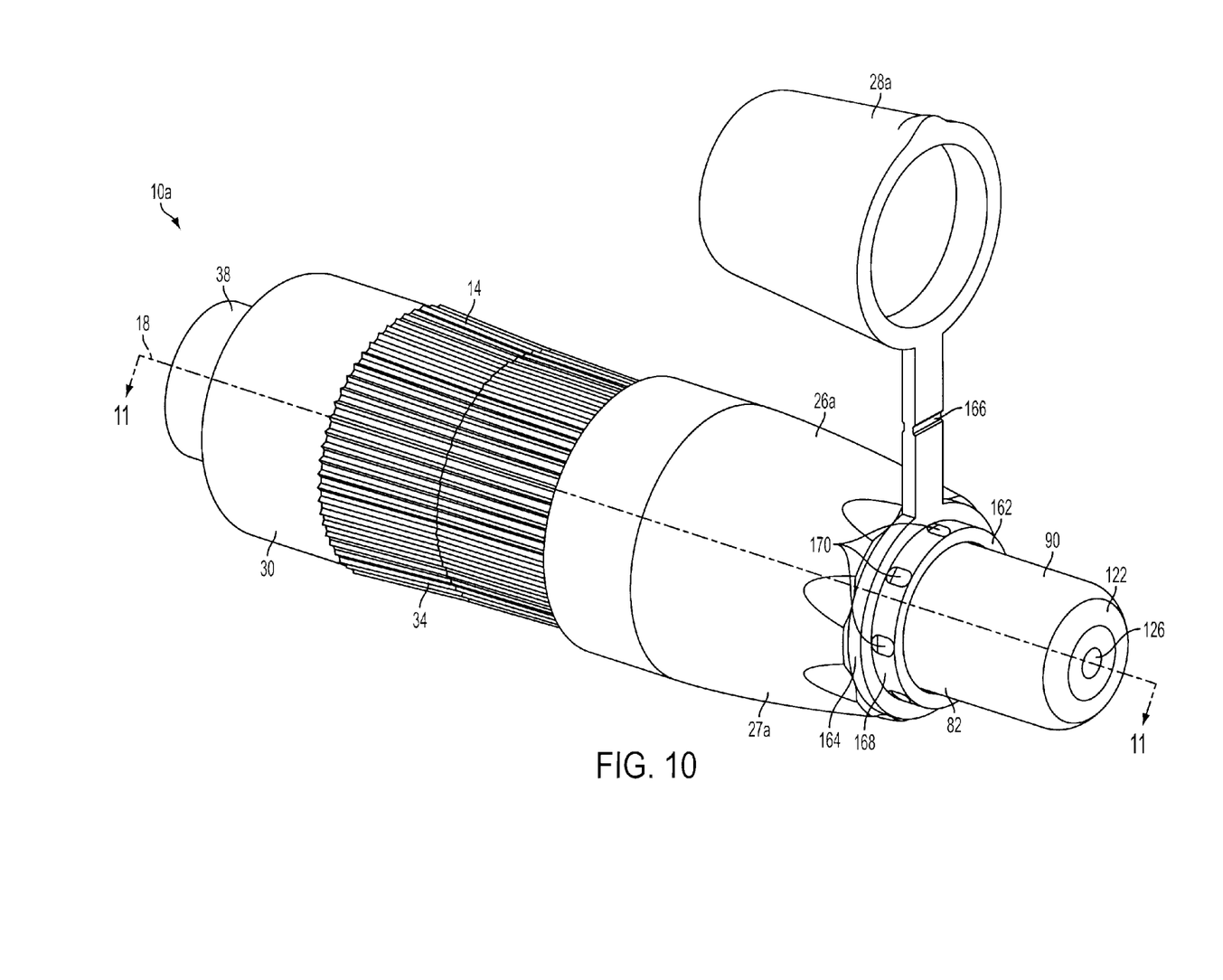
FIG. 10 is a perspective view illustrating an alternative needle cover assembly including a two-piece dosing cap with a tip cap in an open position.
Figure 11:
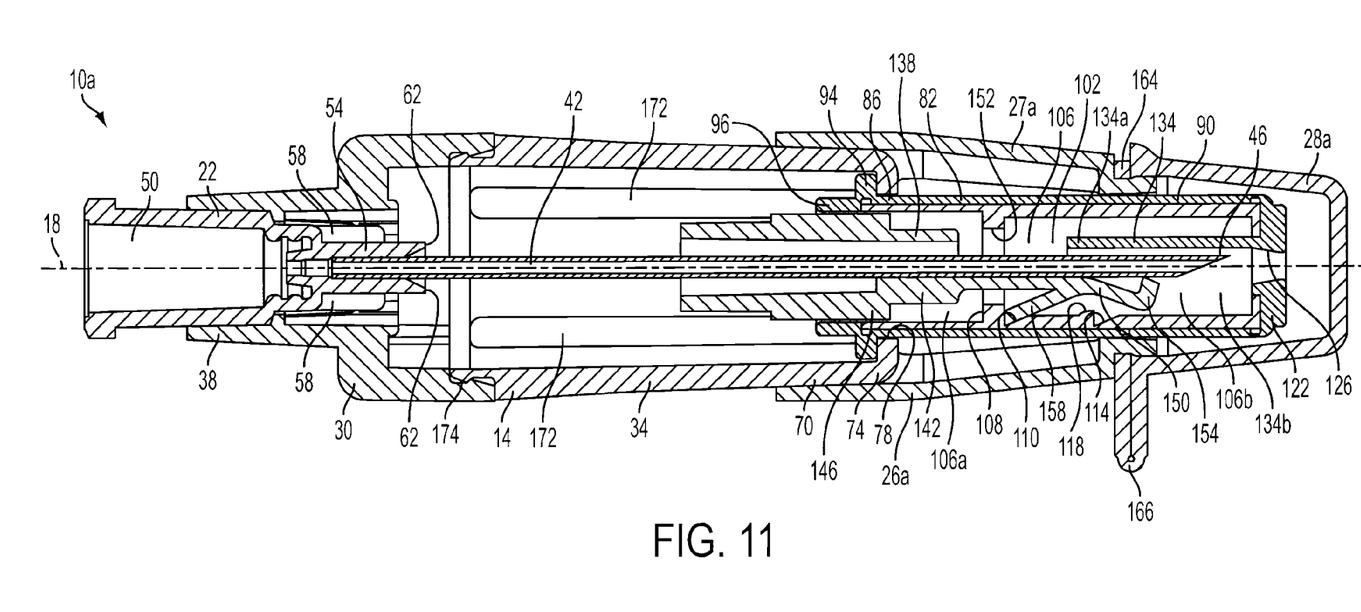
FIG. 11 is section view taken along line 11-11 of FIG. 10 and illustrating the alternative needle and needle cover assembly including the two-piece dosing cap with the tip cap in place and covering the end of the needle sleeve.
Figure 12:
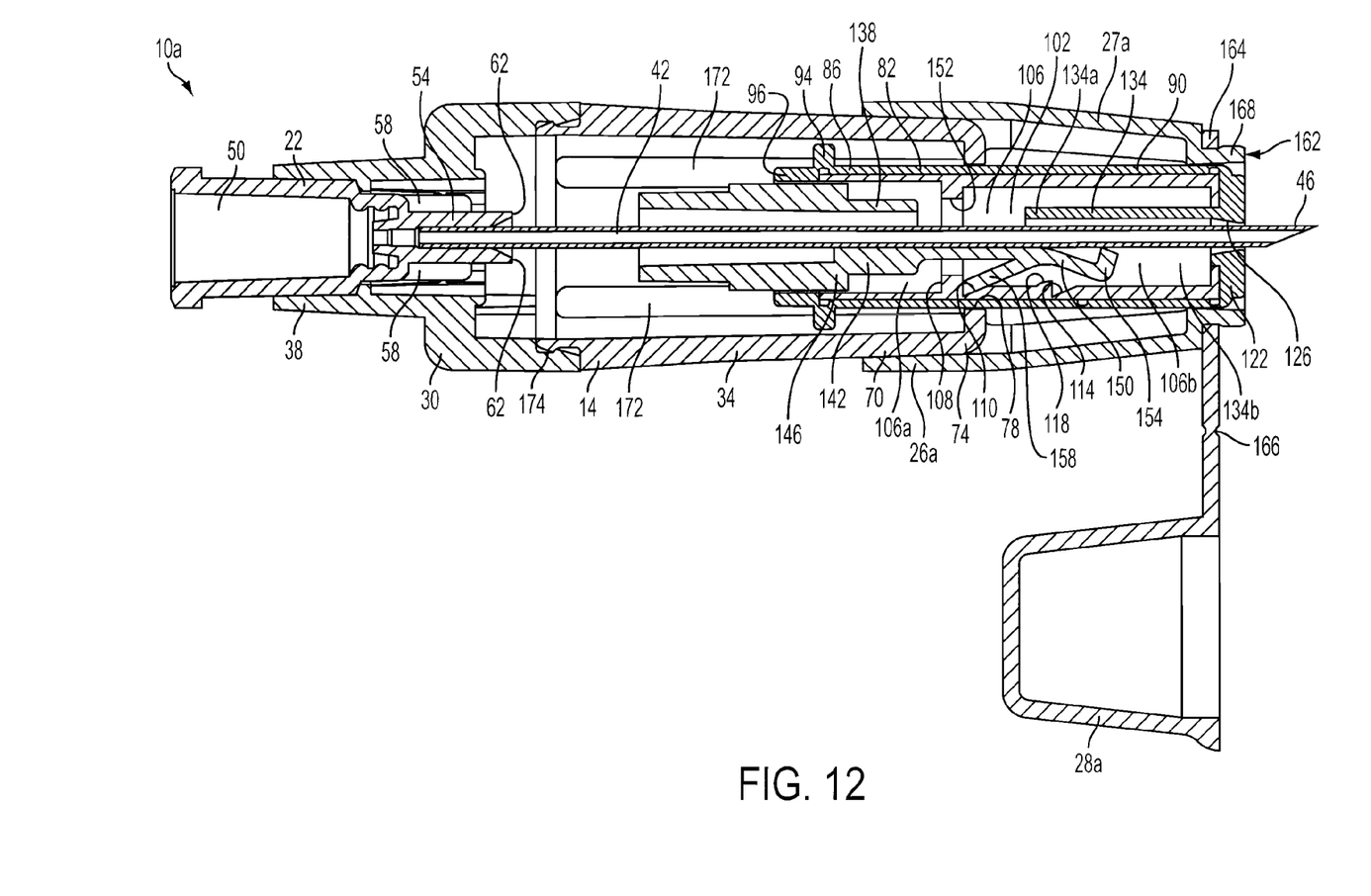
FIG. 12 is a section view similar to FIG. 11 and illustrating the alternative needle and needle cover assembly including the two-piece dosing cap with the tip cap in the open position and the needle sleeve and locking collar retracted to a first retracting position for extraction of a dose from a vial.

FIGS. 10-12 also illustrate an alternative embodiment of the cap 26, identified as cap 26a in FIGS. 10-14, that may be used to prohibit retraction of the needle sleeve 82 beyond the position illustrated in FIG. 5 during the withdrawal of a dose from a vial prior to an injection. As discussed above, retraction of the needle sleeve 82 beyond the position illustrated in FIG. 5 moves the locking collar 138 into a locked position. Thus, if a user is unfamiliar with the syringe assembly 10/10a and is unaware of the significance of the detent resistance provided by engagement of the latching tab 158 and the ramp 118 during retraction, the user may inadvertently insert the needle 42 too far into the vial such that, upon extraction of the needle 42 from the vial, the needle sleeve 82 would be locked in the extended position, thereby preventing injection of the newly withdrawn dose.

As shown in FIGS. 10-12 the cap 26*a* includes a base cap portion 27*a* removably coupled to the end 70 of the housing 14, and a tip cap portion 28*a* that is removably coupled to the base cap 27*a*. Specifically, the tip cap portion 28*a* is connected to a ring portion 164 by a living hinge 166. The living hinge 166 allows the tip cap portion 28*a* to pivot between an open position (FIG. 10) and a closed position (FIG. 11). The ring portion 164 fits over a collar 168 defined on an end of the base cap portion 27*a*. The collar 168 includes a plurality of radially outwardly extending protrusions 170 that allow the ring portion 164 to be installed on and removed from the collar 168 if so desired, but that hold the ring portion 164 in place during normal use of the cap 26*a* during dosing and injection procedures. The protrusions 170 also provide a slight interference fit with the tip cap portion 28*a* to secure the tip cap portion 28*a* in the closed position. In alternative constructions, the base cap portion 27*a* and tip cap portion 28*a* may be formed as a single piece. With the base cap 27*a* coupled to the housing 14 and the tip cap 28*a* in the closed position, the cap 26*a* completely covers the needle sleeve 82 to prevent or substantially prevent contamination of the needle 42 and needle sleeve 82, while also preventing retraction of the needle sleeve 82.

To draw a dose, a user moves the tip cap portion 28*a* to the open position, thereby exposing the outer end 90 of the needle sleeve 82 (FIG. 10). The user then inserts the needle 42 into a vial (not shown) until an end surface 162 of the base cap portion 27*a* engages the vial, thereby prohibiting retraction of the needle sleeve 82 beyond a dosing position, which is illustrated in FIG. 12. The end surface 162 of the base cap portion 27*a* is positioned to allow the needle sleeve 82 to retract a distance sufficient to expose the distal tip 46 of the needle 42 for drawing a dose from the vial, while preventing the needle sleeve 82 from retracting far enough to move the locking collar 138 into the locked configuration.

After withdrawal of the dose from the vial, the user removes the needle 42 from the vial and the needle sleeve 82 moves back to the fully extended position. The user may then move the tip cap portion 28*a* back to the closed position (FIG. 11) for transportation or storage of the dosed syringe prior to an injection or, if the injection is to occur promptly after dosing, the user may remove the entire cap 26*a* to expose the remainder of the needle sleeve 82, thereby readying the syringe and cover assembly 10 to administer the injection to a patient in the manner described above.

It should be appreciated that the base cap portion 27*a* may be removably coupled to the housing 14 by any suitable methods, including snap fits, screw fits, friction fits, and the like. Similarly, the tip cap portion 28*a* and the ring portion 164 may be removably coupled to the base cap portion 27*a*, using suitable known methods, such as snap fits, screw fits, friction fits, and the like.

Figure 13:
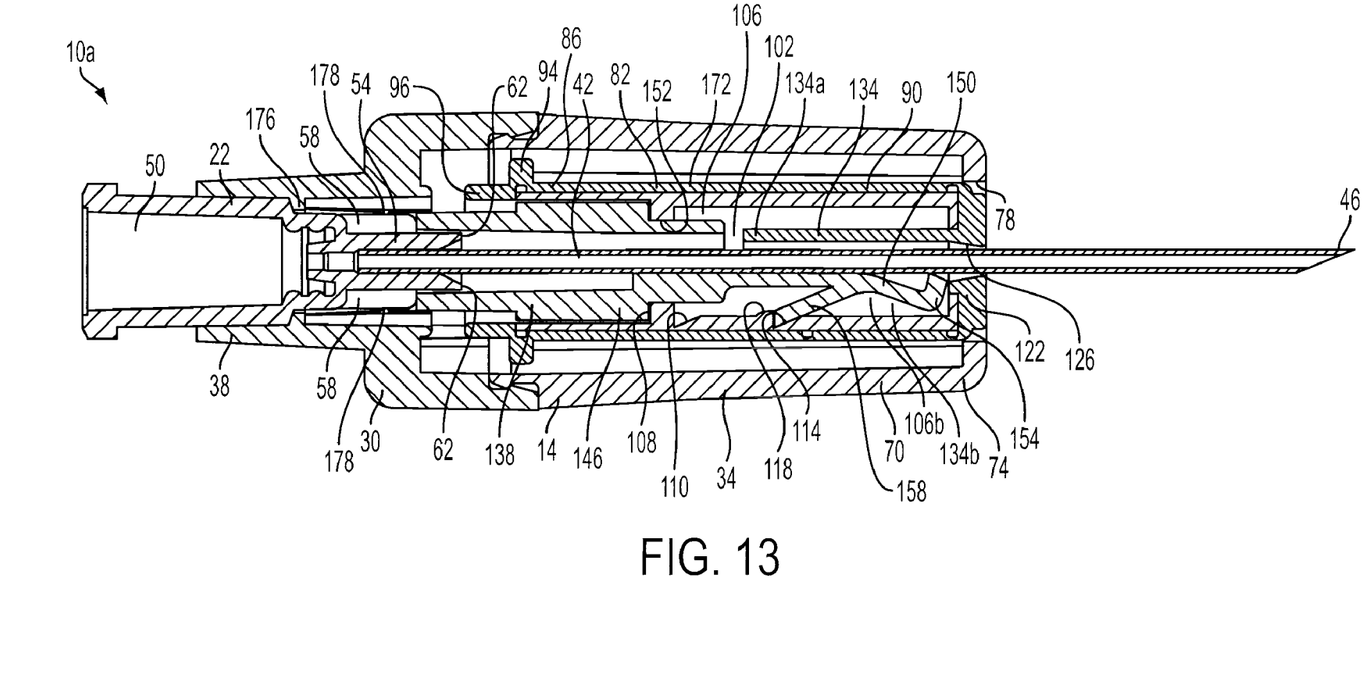
FIG. 13 is a section view similar to FIG. 11 and illustrating the needle sleeve in a retracted position similar to that illustrated in FIG. 6, in which the locking collar has become coupled for axial movement with the needle sleeve.
Figure 14:
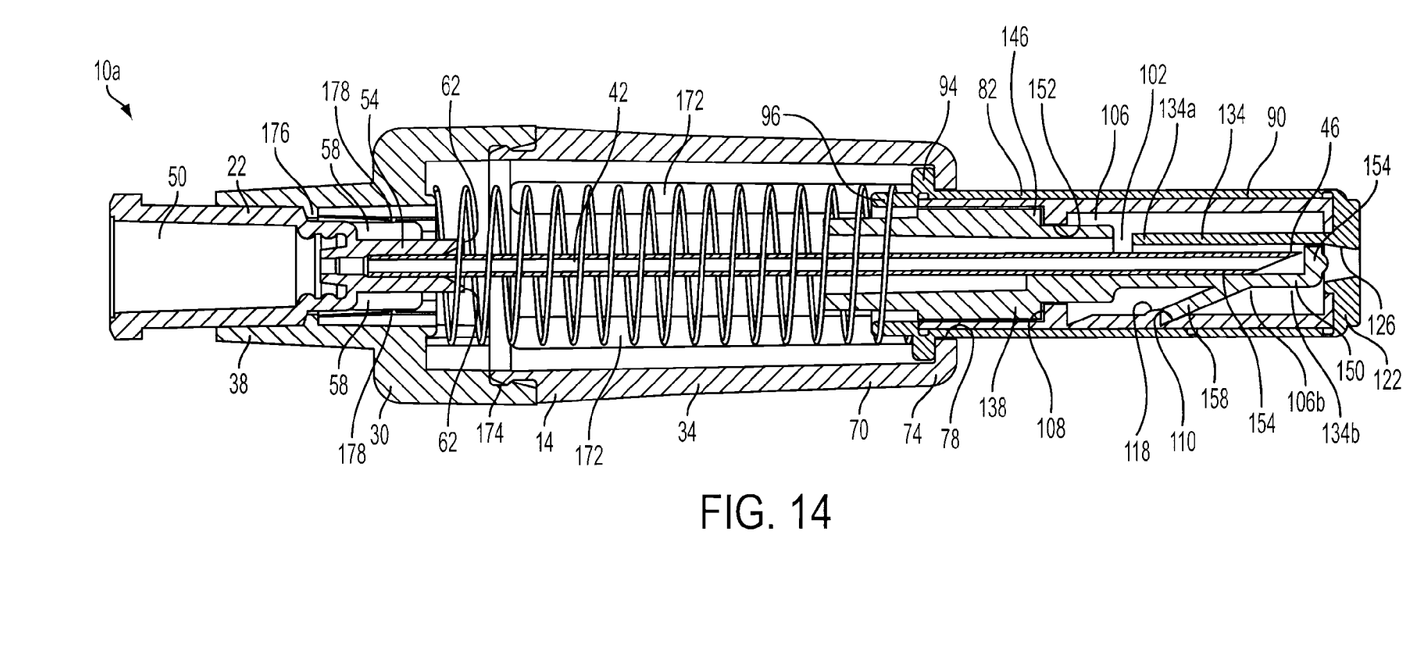
FIG. 14 is a section view similar to FIG. 11 and illustrating the needle sleeve and locking collar in a use-prevention, second extended configuration.

With reference also to FIGS. 11, 13 and 14, it can be seen that the alternative embodiment of the cover assembly 10*a* operates in substantially the same way as the cover assembly 10. FIG. 11 illustrates the cover assembly 10*a* in the ready-for-use configuration with the locking collar 138 in the first position, similar to FIG. 2. FIG. 13 illustrates the needle sleeve 82 substantially fully retracted within the housing 14, and the locking collar 138 has moved to the second position via engagement with the needle hub 22, similar to FIG. 6. Finally, FIG. 14 illustrates the cover assembly 10*a* with sleeve 82 returned to the fully extended position and the foot 154 in the use-prevention position, similar to FIG. 9.

In addition to the features and components discussed above with respect to the cover assembly 10, the lower portion 34 of the housing 14 of the cover assembly 10*a* includes axially and radially inwardly extending ribs 172. The ribs 172 are received in corresponding notches (not shown) formed in the flange 94 of the sleeve 82. Engagement between the ribs 172 and the notches substantially prevents relative rotation between the sleeve 82 and the housing 14. Also, the upper and lower housing portions 30, 34 of the cover assembly 10*a* are coupled by a snap fit connection 174 positioned proximal the needle hub 22. The upper housing portion 30 also includes a plurality of barbs 178 that engage the ribs 58 of the needle hub 22. The barbs 178 are configured to allow insertion of the needle hub 22 into the neck 38 of the upper housing portion 30 but to prevent extraction of the needle hub 22 from the neck 38. The neck 38 is also provided with a shoulder 176 that in some configurations limits axial insertion of the needle hub 22 into the neck 38 such that the ribs 58 are appropriately positioned relative to the housing 14 to affect movement of the locking collar 138 from the first position to the second position, as discussed above.

The locking collar 138 of the cover assembly 10*a* includes an extended flange 146 relative to the locking collar 138 of the cover assembly 10. The extended flange 146 extends further toward the needle hub 22, which compensates for the fact that the needle hub 22 of the cover assembly 10*a* does not extend as far into the housing as the needle hub 22 of the cover assembly 10. Also, as illustrated, the sleeve 82 of the cover assembly 10*a* is formed of multiple pieces, whereas the sleeve 82 of the cover assembly 10 is formed as a single piece.

As discussed above, the needle sleeve 82 is biased to extend from the housing and cover the needle 42 substantially any time the needle is not inserted into a vial or container for loading the syringe, or into the skin or tissue of a patient during an injection. The cover assembly 10 thereby eliminates the periods of needle exposure that occur with many conventional syringes and syringe shields before loading of the syringe, between loading of the syringe and the injection procedure, and after the injection procedure. Eliminating needle exposure also hides the needle from view throughout the injection procedure, thereby reducing anxiety and fear in patients. Furthermore, once the injection procedure is complete, the needle sleeve 82 automatically extends to cover the needle 42 and is locked in the fully extended position by the locking collar 138, thereby preventing subsequent use of the needle 42.

The invention claimed is:

1. A needle cover apparatus for attachment to a syringe needle, the needle defining an axis and having a distal tip, the apparatus comprising:

a base;

a sleeve supported by the base and including a distal end defining an opening, the sleeve axially moveable only once relative to the needle from an extended position wherein the distal tip does not extend through the opening, to a retracted position wherein the distal tip extends through the opening, and back to the extended position, the sleeve biased toward the extended position; and a locking member moveable relative to the sleeve and including a locking portion that, in response to movement of the sleeve from the retracted position to the extended position, moves to cover the opening, thereby preventing subsequent movement of the sleeve to the retracted position;

wherein the locking member moves axially with the sleeve from the extended position toward the retracted position, wherein as the sleeve reaches the fully retracted position the locking member moves axially relative to the sleeve to a locked position in which the locking member is substantially axially fixed relative to the sleeve, wherein the locking member moves axially with the sleeve from the retracted position back to the extended position, wherein the locking member includes a latching tab and the sleeve includes a first recess and a second recess distal of the first recess, wherein the latching tab engages the first recess to axially couple the sleeve and the locking member during movement of the sleeve and the locking member from the extended position toward the retracted position, wherein the latching tab is disengaged from the first recess and moved into engagement with the second recess when the locking member moves to the locked position, and wherein the latching tab engages the second recess to axially couple the sleeve and the locking member during movement of the sleeve and the locking member from the retracted position back to the extended position.

2. The apparatus of claim 1, wherein movement of the sleeve from the extended position to the retracted position moves the locking member relative to the sleeve from a first position to a second position.

3. The apparatus of claim 1, wherein prior to movement of the sleeve from the extended position to the retracted position, the locking portion is positioned proximal of the distal tip, and wherein subsequent to movement of the sleeve from the retracted position back to the extended position, the locking portion is positioned distal of the distal tip between the distal tip and the opening.

4. The apparatus of claim 1, wherein the sleeve is axially moveable between the extended position and a partially retracted position without causing movement of the locking member relative to the sleeve such that the locking portion does not move to cover the opening and thereby allowing repeated movement of the sleeve between the extended position and the partially retracted position, wherein the distal tip extends through the opening in the partially retracted position.

5. The apparatus of claim 4, further comprising a cap assembly including a cap base removably coupled to the base and covering a portion of the sleeve when the sleeve is in the extended position, and a cap tip including at least a portion removably coupled to the cap base and covering the opening of the sleeve when the sleeve is in the extended position and the cap tip is coupled to the cap base, wherein when the cap tip is removed from the cap base, the cap base permits movement of the sleeve from the extended position to the partially retracted position to expose the distal tip, and prevents movement of the sleeve beyond the partially retracted position to the retracted position.

6. The apparatus of claim 1, wherein the sleeve defines a needle cavity that receives the locking member, the locking member including a body surrounding the needle, a resilient arm extending distally from the body, and a foot formed on an end of the resilient arm and defining the locking portion, wherein the locking member is moveable relative to the sleeve from a first position to a second position in response to movement of the sleeve from the extended position to the retracted position.

7. The apparatus of claim 6, wherein the foot is positioned proximally of the distal tip, engages an outer surface of the needle, and is thereby offset from the axis until the sleeve moves back to the extended position with the locking member in the second position, and wherein as the foot moves distally beyond the distal tip, the resilient arm biases the foot into axial alignment with the opening to cover the opening.

8. The apparatus of claim 1, wherein the sleeve is biased toward the extended position by a spring.

9. The apparatus of claim 8, wherein the spring is a progressive spring.

10. The apparatus of claim 1, wherein the locking member is fabricated as one piece.

11. The apparatus of claim 1, wherein the locking member is fabricated from a single material.

12. The apparatus of claim 1, further comprising a cap removably coupled to the base and covering the sleeve when the cap is coupled to the base, the cap including indicia for distracting a child patient.

13. The apparatus of claim 12, wherein the cap is fabricated to resemble a cartoon character.

\* \* \* \* \*